Figure 1:
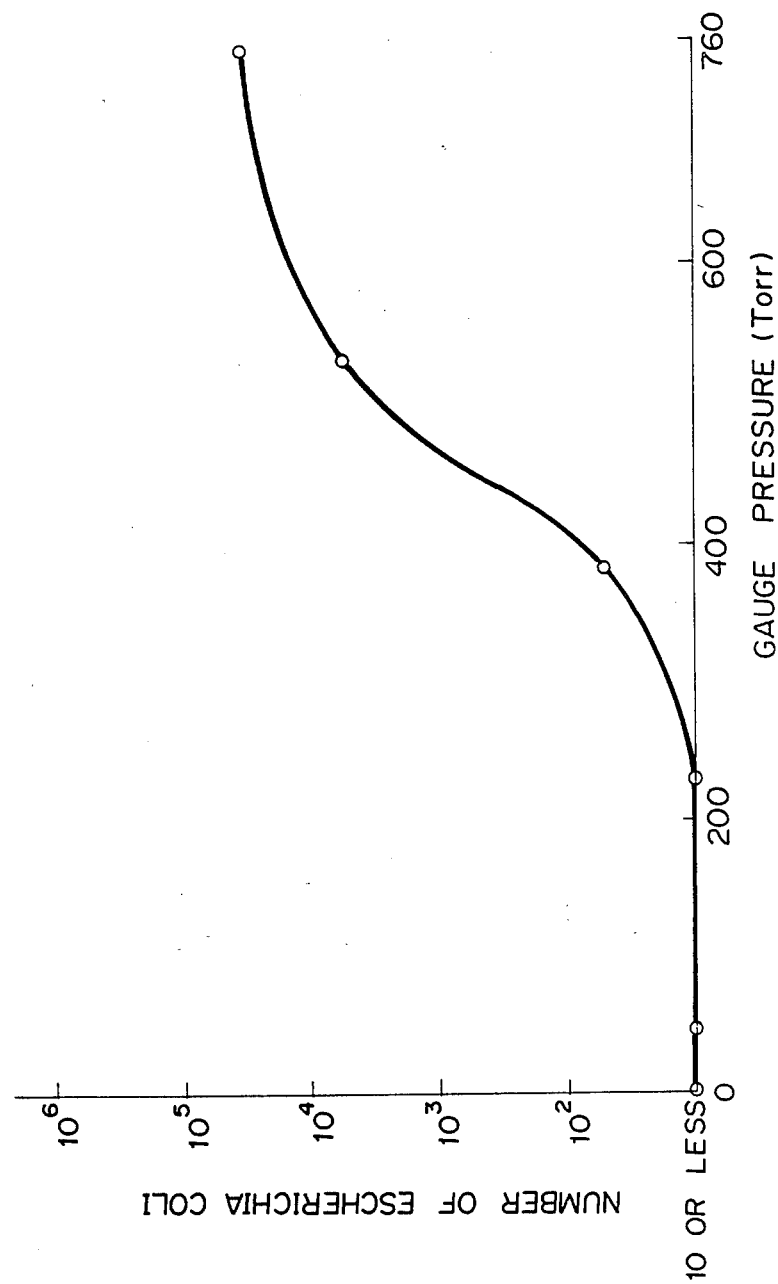

United States Patent [19]

Yamamoto et al.

[11] Patent Number: 4,906,464

[45] Date of Patent: Mar. 6, 1990

[54] METHOD FOR PREPARING DISPERSIONS CONTAINING ANTIBIOTIC POWER

[75] Inventors: Tatuo Yamamoto, Inazawa; Masashi Uchida, Nagoya; Yasuo Kurihara, Nagoya; Ichiro Nakayama, Nagoya, all of Japan

[73] Assignees: Shinagawa Fuel Co., Ltd.; Shinanen New Ceramic Corporation, both of Japan

[21] Appl. No.: 288,025

[22] Filed: Dec. 21, 1988

[30] Foreign Application Priority Data

Dec. 26, 1987 [JP] Japan .................................. 62-331112

[51] Int. Cl.$^4$ ..................... A61K 31/74; A01N 59/16; C08J 6/00; C08J 11/00; C09D 5/00

[52] U.S. Cl. ......................................... 424/78; 424/79; 424/618; 424/641; 424/644; 424/688; 424/617; 424/719; 523/122; 523/218; 523/340; 525/450; 521/27

[58] Field of Search ................. 424/79, 132, 140, 145, 424/157, 131, 166, 78, 81, 80; 523/122, 218, 340; 521/27; 524/450

[56] References Cited

U.S. PATENT DOCUMENTS 4,775,585  10/1988  Hagawara et al. ................. 424/403

FOREIGN PATENT DOCUMENTS

| | | |
|---|---|---|
| 13-4422 | 8/1938 | Japan . |
| 52-92000 | 8/1977 | Japan . |
| 55-38358 | 3/1980 | Japan . |
| 55-264236 | 12/1980 | Japan . |
| 57-77022 | 5/1982 | Japan . |
| 59-37956 | 3/1984 | Japan . |
| 59-133235 | 7/1984 | Japan . |
| 60-64611 | 4/1985 | Japan . |
| 60-79433 | 6/1985 | Japan . |
| 60-100504 | 6/1985 | Japan . |
| 60-136795 | 9/1985 | Japan . |
| 60-136796 | 9/1985 | Japan . |
| 60-174707 | 9/1985 | Japan . |
| 60-178810 | 9/1985 | Japan . |
| 60-181002 | 9/1985 | Japan . |
| 60-181370 | 9/1985 | Japan . |
| 60-184325 | 9/1985 | Japan . |
| 60-202162 | 10/1985 | Japan . |
| 61-137564 | 6/1986 | Japan . |
| 61-138647 | 6/1986 | Japan . |
| 61-138658 | 6/1986 | Japan . |
| 61-138795 | 6/1986 | Japan . |
| 61-103401 | 7/1986 | Japan . |
| 61-232253 | 10/1986 | Japan . |
| 62-7746 | 1/1987 | Japan . |
| 62-7747 | 1/1987 | Japan . |
| 62-7748 | 1/1987 | Japan . |
| 62-70221 | 3/1987 | Japan . |
| 62-195037 | 8/1987 | Japan . |
| 62-195038 | 8/1987 | Japan . |
| 62-41775 | 9/1987 | Japan . |
| 62-238900 | 10/1987 | Japan . |
| 62-241932 | 10/1987 | Japan . |
| 62-241939 | 10/1987 | Japan . |
| 62-243665 | 10/1987 | Japan . |

Primary Examiner—Joseph L. Schofer
Assistant Examiner—Carmen B. Pili-Curtis
Attorney, Agent, or Firm—Jacobs & Jacobs

[57] ABSTRACT

A method for preparing a dispersion containing antibiotic powder comprises mixing the antibiotic powder and a dispersing medium at a temperature at which the dispersing medium is in the form of a liquid under a reduced pressure of not more than 470 Torr. According to this method, the antibiotic powder is uniformly dispersed in various dispersing mediums and antibiotic products having high antibiotic action is effectively be provided by using the resulting dispersion.

10 Claims, 1 Drawing Sheet

METHOD FOR PREPARING DISPERSIONS CONTAINING ANTIBIOTIC POWER

BACKGROUND OF THE INVENTION 1. (Field of the Invention)

The present invention relates to a method for preparing dispersions containing antibiotic powder and more specifically to a method for preparing dispersions capable of imparting antibiotic properties to a polymer or the like.

2. (Description of the Prior Art)

It has been known to incorporate an antibiotic zeolite or the like into a resin to impart antibiotic action thereto (see, for instance, Japanese Patent Un-examined Publication (hereunder referred to as "J.P. KOKAI") No. 59-133235 and Japanese Patent Publication for Opposition Purpose (hereinafter referred to as "J.P. KOKOKU") No. 61-22977).

The inventors of this invention recognized that when an antibiotic zeolite or the like is admixed with a resin, the antibiotic action of the resultant resin varies depending on the conditions of mixing the resin and the antibiotic zeolite and have conducted various studies in this regard.

As a result, they found that the antibiotic action of a resin is enhanced by dispersing an antibiotic powder such as antibiotic zeolite and antibiotic amorphous aluminosilicate in a resin without causing localization of the antibiotic powder at the surface of the resin. In other words, they found that the antibiotic action of a resin in which antibiotic powder is dispersed is enhanced by uniformly dispersing the powder throughout the resin.

However, J.P. KOKAI No. 59-133235 and J.P. KOKOKU No. 61-22977 cited above do not disclose or teach a method for uniformly dispersing an antibiotic powder such as antibiotic zeolite powder in a resin.

J.P. KOKAI No. 57-177033 discloses a method for improving stability, workability and release characteristics of a resin by kneading zeolite powder into the resin. However, while this publication defines the amount of zeolite to be incorporated into the resin, it does not disclose a method for kneading zeolite into the resin in good quality state of dispersal.

SUMMARY OF THE INVENTION

Accordingly, a principal object of the present invention is to provide a method for uniformly dispersing antibiotic powder such as antibiotic zeolite and antibiotic amorphous aluminosilicate in a dispersing medium such as a resin.

Another object of the present invention is to provide a method for dispersing antibiotic powder in a dispersing medium such as a resin, which makes it possible to provide a resin dispersion in which antibiotic powder is dispersed and which shows high antibiotic action.

The aforementioned objects of the present invention can effectively be achieved by providing a method for preparing a resin dispersion containing antibiotic powder. The method comprises mixing a dispersing medium (such as a resin) and antibiotic powder at a temperature at which the dispersing medium is in the form of a liquid, under a reduced pressure of not more than 470 Torr.

DETAILED EXPLANATION OF THE INVENTION

The method of the present invention will now be described in more detail.

The term "antibiotic powder" used herein means a powder of a substance having antibiotic properties or a powder comprising powder of a carrier such as an inorganic or organic carrier on which a substance having antibiotic properties is applied. Specific examples thereof are antibiotic zeolite and antibiotic amorphous aluminosilicate. As the antibiotic zeolite, there can be used any zeolite whose ion-exchangeable ions are exchanged with antibiotic metal ions and/or ammonium ions such as those disclosed in J.P. KOKAI Nos. 59-133235, 60-1810023 and 59-37956 and Japanese Patent Application Ser. (hereunder referred to as "J.P.A.") No. 61-290144 without any restriction. On the other hand, examples of the antibiotic amorphous aluminosilicate include amorphous aluminosilicate whose ion-exchangeable ions are replaced with antibiotic metal ions and/or ammonium ions as disclosed in J.P. KOKAI No. 61-174111.

In the present invention, the antibiotic powder can, for instance, be antibiotic zeolite obtained by partially or completely exchanging the ion-exchangeable ions thereof (e.g., sodium, potassium, calcium, magnesium and/or iron ions) with ammonium or antibiotic metal ions.

The zeolite used herein can be a naturally occurring or synthetic one. Zeolite is in general an aluminosilicate having a three-dimensional skeletal structure and is usually represented by the general formula:

$$XM_{2/n}O—Al_2O_3—YSiO_2—ZH_2O$$

wherein M represents an ion-exchangeable ion and in general a mono- or di-valent metal ion; n is the atomic valency of the ion M; X and Y represent coefficients of the metal oxide and silica respectively; and Z is the water of crystallization number.

Examples of such zeolites include A-type zeolites, X-type zeolites, Y-type zeolites, T-type zeolites, high-silica zeolites, sodalite, mordenite, analcite, clinoptilolite, chabazite and erionite. However, it should be appreciated that the present invention be not restricted to these specific examples.

The ion-exchange capacities of these exemplified zeolites are as follows: A-type zeolite=7 meq./g; X-type zeolites=6.4 meq./g; Y-type zeolites=5 meq./g; T-type zeolites=3.4 meq./g; sodalite=11.5 meq./g; mordenite=2.6 meq./g; analcite=5 meq./g; clinoptilolite=2.6 meq./g; chabazite=5 meq./g; and erionite=3.8 meq./g. Thus, all the zeolites listed above have ion-exchange capacities sufficient to undergo ion-exchange with antibiotic metal and/or ammonium ions. These zeolites can be used in the invention alone or in combination.

Examples of the antibiotic metal ions include silver, copper, zinc, mercury, tin, lead, bismuth, cadmium, chromium or thallium ions and preferably silver, copper, and/or zinc ions.

From the viewpoint of antibiotic action, the amount of these antibiotic metal ions to be added to zeolite ranges from 0.1 to 15%. More specifically, preferred antibiotic zeolite contains 0.1 to 15% of silver ions and 0.1 to 8% of copper or zinc ions. On the other hand, ammonium ions may be included in zeolite in an amount of up to 20%, but from the viewpoint of effectively preventing color change of the zeolite, it preferably ranges from 0.5 to 5% and more preferably 0.5 to 2%. In this specification, "%" means "% by weight" on the basis of the weight measured after drying at 110° C.

Methods for preparing such antibiotic zeolites employed in the present invention will now be detailed below.

The antibiotic zeolite used in the invention can be obtained by bringing zeolite into contact with a previously prepared aqueous mixed solution containing antibiotic metal ions such as silver, copper and zinc ions and optionally ammonium ions to cause ion-exchange between ion-exchangeable ions present in zeolite and the aforesaid antibiotic metal ions and/or ammonium ions. The contact between these ions and zeolite can be carried out according to a batch method or a continuous method (such as a column method) at a temperature of from 10° to 70° C., preferably 40° to 60° C., for 3 to 24 hours, preferably 10 to 24 hours. During the contact, the pH value of the aqueous mixed solution is adjusted to 3 to 10, preferably 5 to 7, to prevent silver oxide or the like from causing deposition on the surface of the zeolite or within pores thereof. In addition, each of the ion species is generally used in the form of a salt to prepare the aqueous mixed solution.

For instance, there may be mentioned such an ammonium ion source as ammonium nitrate, ammonium sulfate, ammonium acetate, ammonium perchlorate, ammonium thiosulfate and ammonium phosphate; such a silver ion source as silver nitrate, silver sulfate, silver perchlorate, silver acetate, diamine silver nitrate and diamine silver sulfate; such a copper ion source as copper(II) nitrate, copper sulfate, copper perchlorate, copper acetate and tetracyan copper potassium; such a zinc ion source as zinc(II) nitrate, zinc perchlorate, zinc acetate, zinc sulfate and zinc thiocyanate; such a mercury ion source as mercury perchlorate, mercury acetate and mercury nitrate; such a tin ion source as tin sulfate; such a lead ion source as lead sulfate and lead nitrate; such a bismuth ion source as bismuth chloride and bismuth iodide; such a cadmium ion source as cadmium perchlorate, cadmium sulfate, cadmium nitrate and cadmium acetate; such a chromium ion source as chromium perchlorate, chromium sulfate, chromium ammonium sulfate, chromium nitrate and chromium acetate; and such a thallium ion source as thallium perchlorate, thallium sulfate, thallium nitrate and thallium acetate.

The content of the above ions such as ammonium ions in the antibiotic zeolite can appropriately be controlled by adjusting the concentration of each ion species (or salt) in the aforesaid aqueous mixed solution. For instance, in a case where the antibiotic zeolite comprises ammonium and silver ions, the antibiotic zeolite having an ammonium content of 0.5 to 5% and a silver ion content of 0.1 to 5% can appropriately be obtained by bringing zeolite into contact with an aqueous mixed solution having an ammonium ion concentration of 0.2 to 2.5 mole/l and a silver ion concentration of 0.002 to 0.15 mole/l. If the antibiotic zeolite further comprises copper and/or zinc ions, the antibiotic zeolite having copper and/or zinc ion contents of 0.1 to 8%, respectively, in addition to silver and/or ammonium ions can appropriately be prepared by employing an aqueous mixed solution containing 0.1 to 0.85 mole/l of copper ions and/or 0.15 to 1.2 mole/l of zinc ions in addition to the foregoing amount of ammonium and silver ions.

Alternatively, the antibiotic zeolite used in the present invention can also be prepared by using separate aqueous solutions each containing single ion species (or salt) and bringing zeolite into contact with each solution one by one to cause ion-exchange therebetween. The concentration of each ion species in a specific solution can be determined in accordance with the concentrations of those ion species in the aforesaid aqueous mixed solutions.

After the ion-exchange treatment, the resultant antibiotic zeolites are sufficiently washed with water, followed by drying. It is preferable to dry the antibiotic zeolites till the residual moisture content in the zeolite reaches about 0.5 to 20%, preferably 1 to 10%. The restriction on the moisture content of the antibiotic zeolite is important to obtain a dispersion having good dispersion properties. For these purposes, it is desirable to dry the zeolite at a temperature ranging from 105° to 115° C. under normal pressure or at a temperature ranging from 70° to 90° C. at a reduced pressure (e.g., about 1 to 30 Torr).

After drying, the antibiotic zeolites thus obtained are pulverized and classified, if necessary. In this respect, it is preferred that the average particle size of the antibiotic zeolites be relatively small, generally in the range of from 0.04 to 20 microns and preferably from 0.1 to 10 microns, for the purpose of obtaining an antibiotic resin dispersion having high antibiotic action.

It is noted that if the ion-exchange is carried out with antibiotic metal ions such as tin or bismuth ions or organic ions which do not have proper water-soluble salt, the ion-exchange can be performed under a condition such that hardly any soluble basic salt is deposited during ion-exchange utilizing an organic solvent such as an alcohol or acetone.

In the method of this invention, it is also possible to use, as antibiotic powder, antibiotic amorphous aluminosilicates (hereinafter referred to as "AAS") whose ion-exchangeable ions are partially or completely exchanged with antibiotic metal ions. AAS used as a starting material is not restricted to specific types and any conventionally known ones can be used in this invention without any further treatment. AAS is in general represented by the formula:

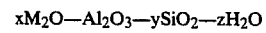

$$xM_2O-Al_2O_3-ySiO_2-zH_2O$$

wherein M is in general an alkali metal such as sodium or potassium and x, y and z represent mole number of the metal oxide, silica and the water of crystallization respectively. Unlike the crystalline aluminosilicate called zeolite, AAS is an amorphous substance which does not show any diffraction patterns in X-ray diffraction analysis and it is thought that it has a structure comprising very fine zeolite crystals formed during processes for preparing AAS (diameter=several tens of angstrom), onto which amorphous substances composed of $SiO_2$, $Al_2O_3$ and $M_2O$ are deposited.

AAS can be prepared by reacting a solution of an aluminum salt, a solution of a silicon compound and a solution of an alkali metal salt each having a desired concentration at a low temperature of not more than 60° C. and then washing the products prior to the start of crystallization. Examples of methods for producing the same are disclosed in, for instance, J.P. KOKOKU No. 52-58099 and J.P. KOKAI No. 55-162418.

AAS obtained by the aforementioned method generally contains alkali metal oxides in an amount of more than 10%. This AAS can be directly used for preparing antibiotic AAS. In the present invention, the content of the alkali metal oxides in the AAS is not critical, but it is particularly preferable to reduce the content of $M_2O$ to 10% or less, preferably 8% or less from the viewpoint of effectively preventing the color change of resins or the like with time when the AAS is incorporated into the resins.

The AAS is ion-exchanged with antibiotic metal ions. Examples of such antibiotic metal ions are silver, copper, zinc, mercury, tin, lead, bismuth, cadmium, chromium and thallium ions and preferably silver, copper and zinc ions.

The amount of silver ions to be added to AAS ranges from 0.1 to 50%, preferably 0.5 to 5% in order to attain excellent antibiotic action. Moreover, it is further preferable to add at least one member selected from the group consisting of copper, zinc, mercury, tin, lead, bismuth, cadmium, chromium and thallium ions in an amount ranging from 0.1 to 10%, in addition to silver ions.

In addition, it is also possible to add ammonium ions to the antibiotic AAS in addition to the foregoing antibiotic metal ions by ion-exchange technique. The antibiotic AAS may contain ammonium ions in an amount of up to 15%, but in general the content of ammonium ions ranges from 0.5 to 5%, preferably 0.5 to 2% for the purpose of effectively preventing color change of AAS.

The antibiotic AAS can, for instance, be prepared according to either of the following two methods:

(1) The antibiotic AAS is prepared by bringing an AAS slurry into contact with antibiotic metal ions to cause ion-exchange between ion-exchangeable ions in AAS and the antibiotic metal ions.

(2) The antibiotic AAS is prepared by preparing a slurry of AAS so that the pH of the slurry is preferably not more than 6 and then bringing AAS in the slurry into contact with antibiotic metal ions to cause ion-exchange between ion-exchangeable ions in AAS and the antibiotic metal ions.

In the method (1), AAS whose $M_2O$ content is preferably not more than 10% is used. Commonly used AAS has an $M_2O$ content of not less than 10%. Thus, the $M_2O$ content of AAS prepared according to the foregoing method can be adjusted by, for instance, suspending the same in water to form a slurry, dropwise adding an aqueous solution of an acid thereto with stirring to neutralize the alkali metals and/or alkaline earth metals present in AAS and to thus adjust the $M_2O$ content to not more than 10%. In this respect, it is preferred to use a dilute acid aqueous solution having a concentration of not more than 0.1N and to adjust the rate of dropwise addition of the acid solution to 100 ml per 30 minutes, although the rate varies depending on the stirring conditions and the scale of the reaction. Further, the neutralization is performed so that the pH value of the slurry ranges from 3 to 6, preferably 4 to 5. Examples of the acids used in the neutralization are an inorganic acid such as nitric acid, sulfuric acid, perchloric acid, phosphoric acid or hydrochloric acid and an organic acid such as formic acid, acetic acid, oxalic acid or citric acid.

The neutralized AAS having an $M_2O$ content of not more than 10% is filtered, washed with water and is directly used in the method (1) as a slurry or it may be further dried to obtain AAS having an $M_2O$ content of not more than 10%.

In the method (1), the AAS slurry having an $M_2O$ content of not more than 10% is admixed with an aqueous mixed solution containing antibiotic metal ions such as silver, copper and/or zinc ions to bringing AAS into contact with the aforesaid antibiotic metal ions to cause ion-exchange between the ion-exchangeable ions present in AAS with the antibiotic metal ions. The contact is performed at a temperature ranging from 5° to 70° C., preferably 40° to 60° C. for 1 to 24 hours, preferably 10 to 24 hours in accordance with either a batch technique or a continuous technique (such as a column method).

Each ion in the aqueous mixed solution is usually in the form of a salt. The same ion sources as those defined above in connection with the method for preparing the antibiotic zeolites can also be used to prepare the antibiotic AAS.

The content of antibiotic metal ions and/or ammonium ions in AAS can be controlled by adjusting the concentration of each ion (or salt) in the aqueous mixed solution. For instance, if the antibiotic AAS contains silver ions, the silver ion content thereof can be controlled to 0.5 to 6% by adjusting the concentration of silver ions in the aqueous mixed solution to 0.01 to 0.30 mole/l. In addition, if the antibiotic AAS contains copper and/or zinc ions in addition to silver ions, the concentrations of copper and zinc in the aqueous mixed solution are controlled to 0.05 to 0.4 mole/l respectively so that antibiotic AAS whose copper and zinc ion contents are 1 to 8% respectively can properly be prepared.

Likewise, the antibiotic AAS used in the method of this invention is also prepared by using separate aqueous solutions each containing single ion species (of salt) and bringing AAS into contact with each solution one by one to cause ion-exchange therebetween. The concentration of each ion species in a specific solution can be determined in accordance with the concentrations of those ion species in the aforementioned aqueous mixed solutions.

After the ion-exchange treatment, the resultant antibiotic AAS is sufficiently washed with water, followed by drying. For example, it is preferable to dry the antibiotic AAS till the residual moisture content in AAS reaches about 0.5 to 20%, preferably 1 to 10%. The restriction on the moisture content of the antibiotic AAS is important for obtaining a dispersion having high dispersion properties. For these purposes, it is desirable to dry AAS at a temperature ranging from 105° to 115° C. under normal pressure or at a temperature ranging from 70° to 90° C. at a reduced pressure (e.g., about 1 to 30 Torr).

After drying, the antibiotic AAS thus obtained is pulverized and classified, if necessary. In this respect, it is preferred that the average particle size of the antibiotic AAS is relatively small and in general ranges from 0.04 to 20 microns and preferably 0.1 to 10 microns for the purpose of obtaining an antibiotic resin dispersion having high antibiotic action.

It is noted that if the ion-exchange is carried out with antibiotic metal ions such as tin or bismuth ions or organic ions which do not have a proper water-soluble salt, the ion-exchange can be performed under a condition such that hardly any soluble basic salt is deposited during ion-exchange utilizing an organic solvent such as an alcohol or acetone.

On the other hand, in the method (2), the $M_2O$ content in AAS can be controlled to not more than 10% by adjusting the pH value of a slurry of AAS obtained by an ordinary method to not more than 6, preferably 3 to 6, and more preferably 4 to 5. In the method (2), the pH adjustment can likewise be performed in the same manner as that described before in connection with the method (1).

AAS in the slurry can be subjected to ion-exchange by admixing the slurry having a controlled pH value and a solution containing antibiotic metal ions and/or ammonium ions. The ion-exchange can be performed in the same manner as that described above in connection with the method (1).

The dispersion of the present invention can be prepared by admixing the aforementioned antibiotic powder and a dispersing medium under desired conditions.

The dispersing mediums used in the invention can be thermoplastic resins, resin emulsions and vehicles commonly utilized in kneading, into a polymer material such as rubber and plastics, a pigment or a filler as in the field of paints. The dispersing mediums must be in liquid state at ordinary temperature or when heated at a low temperature at which they are not decomposed. Specific examples thereof are polystyrene resin, polyurethane resin, vinyl chloride resin, nylon resin, acrylic resin, polyvinylidene chloride, polyols such as ester type polyols and ether type polyols, polyvinyl alcohol, alcohols such as ethylene glycol, glycerin and derivatives thereof (e.g., ethylene glycol dimethyl ether and glycerol diglycidyl ether), higher alcohols such as lauryl alcohol, oleyl alcohol and orristearyl alcohol, higher fatty acids such as lauric acid, mylistic acid, palmitic acid, stearic acid, oleic acid and behenic acid. In addition, examples of the resin emulsions are those obtained by dispersing (or emulsifying) a resin such as polyvinyl acetate, polyacrylate, epoxy resin or urethane resin in a dispersing medium such as water or hydrocarbon type compounds or a synthetic rubber latexes.

Moreover, in the invention, it is also possible to provide antibiotic paints by utilizing known paints such as oil paints, lacquer, varnish, alkyl resin type, aminoalkid resin type, vinyl resin type, acrylic resin type, epoxy resin type, urethane resin type, water type, chlorinated rubber type and phenol type paints.

In the present invention, the antibiotic powder and the dispersing medium are mixed at a temperature at which the latter is in the form of liquid under a reduced pressure of not more than 470 Torr, preferably not more than 400 Torr and more preferably not more than 250 Torr. The antibiotic powder can be uniformly dispersed into the dispersing medium by mixing these under such conditions and the resultant dispersion shows high antibiotic action. Moreover, it is desirable to adjust the viscosity (at 25° C.) of the mixture of the antibiotic powder and the dispersing medium to 2,000 to 200,000 cP, preferably 5,000 to 100,000 cP for the purpose of obtaining the intended dispersion within a relatively short period of time.

In the method of the present invention, a variety of mixers can be used and examples thereof include a Banbury type mixer, a two-roll mill and a kneader which can provide high shear dispersion force; and a three-roll mill, a colloid mill, a mixer, sand mill and ball mill which can provide a low shear dispersion force. Among these, particularly preferred in the invention are a ball mill, a mixer, a roll mill and a kneader because in these apparatuses, the operations for reducing pressure are easily performed.

The dispersions containing antibiotic powder, which can be prepared according to the method of the present invention, are applicable in a variety of fields. For instance, they can be used for directly coating cloths and forming a resin coating or injecting these immediately before the nozzle during spinning to form antibiotic fibers in the field of fabrics. In addition, it is also possible to obtain antibiotic films or molded articles from a dispersion system in which a thermoplastic resin is used as the dispersing medium.

As discussed above in detail, the method for preparing dispersions containing antibiotic powder according to the present invention makes it possible to uniformly disperse the antibiotic powder such as antibiotic zeolite in resins without causing association and it is possible to provide resins exhibiting high antibiotic action starting from the resultant dispersions.

The method of the present invention will hereunder be explained in more detail with reference to the following non-limitative working Examples and the effects practically achieved by the present invention will also be discussed in detail.

EXAMPLE 1

Test on Antibiotic Action of Plates Obtained from Thermoplastic Resins

Antibiotic Y-type zeolite (1.4 kg; moisture content=5.3%) having a composition of $0.11Ag_2O\text{-}0.75(NH_4)_2O\text{-}0.6Na_2O\text{-}Al_2O_3\text{-}4.5SiO_2$ was introduced into a double-arm kneader (inner volume=10 liters) provided with a jacket and then 4.1 kg of polystyrene resin (DIC Styrene GH-6300 available from DAINIPPON INK AND CHEMICALS, INC.) was introduced thereinto. Then, the ingredients were premixed at a speed of 50 rpm and a temperature of 200° C. for 30 minutes. At this stage, the viscosity of the resultant slurry was 12900 cP. The kneader was closed, followed by reducing the inner pressure thereof to a desired value by operating a rotary vacuum pump and kneading the slurry at 50 rpm and 200° C. for 60 minutes while applying a shearing force. The resultant dispersion was formed into plates having a size of 73×44×2 mm by means of an injection molder. 15 ml of a solution containing *Escherichia coli* ($10^5$ cells/ml) was sprayed onto the resultant plates and was cultured at 37° C. for 24 hours. The bacteria solution was washed away with physiological saline and the number of bacteria cells (*Escherichia coli*) present in the wash liquid was determined. The results are summarized in Table I below and shown in FIG. 1 attached hereto.

TABLE I

| Test No. | Pressure (Torr) | Number of cells of *Escherichia coli* |
| --- | --- | --- |
| C-1 | 760 | $2 \times 10^4$ |
| C-2 | 530 | $7 \times 10^3$ |
| C-3 | 380 | $6 \times 10$ |
| C-4 | 230 | not more than 10 |
| C-5 | 50 | not more than 10 |
| C-6 | 1 | not more than 10 |
| C-7 | 0.1 | not more than 10 |

The results shown in FIG. 1 indicate that in the method of the invention, if the pressure is reduced to not more than 470 Torr, the number of cells of *Escherichia coli* becomes extremely low compared with those observed when the mixing is performed at ordinary pressure. Moreover, as the pressure is controlled to not more than 400 Torr and further to not more than 250 Torr, the number of *Escherichia coli* cells can further be reduced.

EXAMPLE 2

Preparation of Antibiotic Zeolite Slurry

Antibiotic Y-type zeolite (1.4 kg; moisture content=5.3%) having a composition of $0.11Ag_2O$-$0.75(NH_4)_2O$-$0.6Na_2O$-$Al_2O_3$-$4.5SiO_2$ was introduced into a double-arm kneader (inner volume=10 liters) provided with a jacket and then 2.6 kg of polyol for paints (Nippolan 1004; available from NIPPON POLYURETHANE CO., LTD.) was introduced thereinto. Then, the ingredients were premixed at a speed of 50 rpm for 30 minutes. At this stage, the viscosity of the resultant dispersion was 56700 cP. The kneader was closed, followed by reducing the inner pressure thereof to a desired value by operating a rotary vacuum pump and kneading the slurry at 50 rpm for 60 minutes while applying a shearing force. The dispersion properties of the resultant dispersion samples were determined by means of a Grain Gauge (0-10 micron; 0-25 micron: available from YOSHIMITSU SEIKI CO., LTD.). The measurement was performed according to JIS K 5400. The results are summarized in Table II below.

TABLE II

| Test No. | Pressure (Torr) | Grain Gauge Found (micron) |
|---|---|---|
| 1-1 | 760 | 25 |
| 1-2 | 530 | 15 |
| 1-3 | 380 | 10 |
| 1-4 | 230 | 2 |
| 1-5 | 50 | 3 |
| 1-6 | 1 | 2 |
| 1-7 | 0.1 | 1 |

As seen from the results obtained above, dispersions exhibiting excellent dispersion properties can be obtained as the degree of pressure reduction during mixing is high.

EXAMPLE 3

Preparation of Antibiotic Amorphous Aluminosilicate Slurry

Antibiotic amorphous aluminosilicate (10 kg; moisture content=2.0%) having a composition of $0.30Ag_2O$-$0.51(NH_4)_2O$-$0.1Na_2O$-$Al_2O_3$-$2.3SiO_2$ was introduced into a ball mill (inner volume=100 liters; available from Mitsui Miike Machinery Co., Ltd. under the trade name of MQ1 Attritor) and then 18.6 kg of polyol for paints (Nippolan 1004; available from NIPPON POLYURETHANE CO., LTD.) was introduced thereinto followed by reducing the inner pressure to a desired value using a vacuum pump. Then, the ingredients were mixed at a speed of 200 rpm and a temperature of 86° C. for two hours. At this stage, the viscosity of the resultant dispersion was 26800 cP. The dispersion properties of the resultant dispersion samples were determined by means of a Grain Gauge (0-10 micron; 0-25 micron: available from YOSHIMITSU SEIKI CO., LTD.) in the same manner as in Example 2. The results are summarized in Table III below.

TABLE III

| Test No. | Pressure (Torr) | Grain Gauge Found (micron) |
|---|---|---|
| B-1 | 760 | 15 |
| B-2 | 530 | 10 |
| B-3 | 380 | 5 |
| B-4 | 230 | not more than 1 |
| B-5 | 50 | not more than 1 |

EXAMPLE 4

Relation Between the Viscosity and Dispersion Properties of the Slurry

The same test as in Example 2 was performed utilizing polyols for paints having a variety of viscosities. The viscosity at room temperature and the maximum pressure at which the grain gauge (N=10) is not more than 5 micron were determined on a 35% antibiotic zeolite mixture with each polyol. The viscosity was measured using a B-type viscometer available from TOKYO KEIKI CO., LTD. was used. The results observed are listed in Table IV.

TABLE IV

| Polyol | Test No. | Viscosity (cP) | Maximum Pressure (Torr) |
|---|---|---|---|
| Nippolan 150 | 2-1 | 2,400 | 380 |
| Nippolan 141 | 2-2 | 5,100 | 230 |
| Nippolan 1004 | 2-3 | 56,700 | 230 |
| Nippolan 125 | 2-4 | 106,000 | 230 |
| Nippolan 121 | 2-5 | 192,000 | 230 |

As seen from the results listed in Table IV, the preferred viscosity of the slurry during kneading ranges from 2,000 to 200,000 cP.

EXAMPLE 5

Test on Antibiotic Action

The slurry composition obtained in Example 2, 3 or 4 (20 g each) was added to 1 kg of polyethylene resin (L 320; available from MITSUBISHI CHEMICAL INDUSTRIES LTD.) and the mixture was formed into polyethylene films of 10 microns thick at 240° C. using a T-die film molding machine. 15 ml of a solution containing *Escherichia coli* ($10^5$ cells/ml) was sprayed onto the resultant film and was cultured at 37° C. for 24 hours. The bacteria solution was washed away with physiological saline and the number of bacteria cells (*Escherichia coli*) present in the wash liquid was determined. The results are summarized in Table V below.

TABLE V

| Test No. | Number of Cells of *Escherichia coli* | Grain Gauge found (micron) |
|---|---|---|
| 1-1 | $8 \times 10^5$ | 25 |
| 1-2 | $4 \times 10^5$ | 15 |
| 1-3 | $7 \times 10^2$ | 10 |
| 1-4 | not more than 10 | 2 |
| 2-4 | not more than 10 | 3 |
| 1-7 | not more than 10 | 1 |
| B-4 | not more than 10 | not more than 1 |

The results shown in Table V indicate that there is a good correlation between the grain gauge found and the antibiotic action (number of *Escherichia coli* cells). As a result, the antibiotic action can be estimated by means of the value of grain gauge found in Examples 2 to 4.

EXAMPLE 6

Test on Antibiotic Action of Cloths to Which the Antibiotic Slurry is Applied The antibiotic zeolite slurries prepared in Examples 2 to 4 were applied to the surface of a variety of cloths in an amount of 0.5% by weight (size of samples=50×50 mm). One ml of a solution containing *Escherichia coli* ($10^5$ cells/ml) was sprayed onto the resultant film and was cultured at 37° C. for 24 hours. The bacteria solution was washed away with physiological saline and the number of bacteria cells (*Escherichia coli*) present in the wash liquid was determined. The results are summarized in Table VI below.

TABLE VI

| Test No. | Kind of Cloth | Number of Cells of *Escherichia coli* | Grain gauge Found(micron) |
|---|---|---|---|
| 1-1 | cotton | $3 \times 10^4$ | 25 |
|  | rayon | $8 \times 10^3$ | 25 |
|  | acrylic | $5 \times 10^2$ | 25 |
| 1-4 | cotton | $2 \times 10$ | 2 |
|  | rayon | not more than 10 | 2 |
|  | acrylic | not more than 10 | 2 |
| B-4 | cotton | not more than 10 | 1 |
|  | rayon | not more than 10 | 1 |
|  | acrylic | not more than 10 | 1 |

The results shown in Table VI indicate that the cloths having excellent antibiotic properties can be obtained by directly applying the dispersion containing antibiotic powder prepared according to the method of the present invention to the surface of a cloth of a synthetic fiber such as rayon or a natural fiber such as cotton.

What is claimed is:

1. A method for preparing a dispersion containing an antibiotic powder, which comprises mixing an antibiotic powder selected from the group consisting of an antibiotic zeolite whose ion-exchangeable ions are partially or completely ion-exchanged with antibiotic metal ions or with ammonium and antibiotic metal ions and an antibiotic amorphous aluminosilicate whose ion-exchangeable ions are partially or completely ion-exchanged with antibiotic metal ions or with ammonium and antibiotic metal ions with a dispersion medium selected from the group consisting of a thermoplastic resin, a polyol, an alcohol, a higher alcohol, a higher fatty acid and a resin emulsion, said mixing being carried out at a reduced pressure of not more than 470 Torr and at a temperature at which said dispersion medium is in the form of a liquid such that the viscosity (at 25° C.) said mixture of antibiotic powder and dispersion medium is adjusted to 2,000 cp. to 200,000 cp.

2. A method as set forth in claim 1 wherein the mixing is carried out under a reduced pressure of not more than 400 Torr.

3. A method as set forth in claim 2 wherein the mixing is carried out under a reduced pressure of not more than 250 Torr.

4. A method as set forth in claim 1 wherein the antibiotic metal ions are ions of at least one metal selected from the group consisting of silver, copper, zinc, mercury, tin, lead, bismuth, cadmium, chromium and thallium.

5. A method as set forth in claim 4 wherein the antibiotic metal ions are silver, copper or zinc ions.

6. A method as set forth in claim 1 wherein the antibiotic metal ions are ions of at least one metal selected from the group consisting of silver, copper, zinc, mercury, tin, lead, bismuth, cadmium, chromium and thallium.

7. A method as set forth in claim 6 wherein the antibiotic metal ions are silver, copper or zinc ions.

8. A method as set forth in claim 1 wherein the thermoplastic resin is at least one member selected from the group consisting of polystyrene resin, polyurethane resin, vinyl chloride resin, nylon resin, acrylic resin and polyvinylidene chloride.

9. A method as set forth in claim 1 wherein the moisture content of the antibiotic powder ranges from 0.5 to 20% by weight.

10. A method as set forth in claim 1 wherein the particle size of the antibiotic powder ranges from 0.04 to 20 microns.

* * * * *